United States Patent [19]

Imamura et al.

[11] Patent Number: 4,491,631
[45] Date of Patent: Jan. 1, 1985

[54] ASSAY METHOD FOR LIPID COMPONENT, ASSAY COMPOSITION, AND PROCESS FOR PRODUCTION OF ENZYME USED THEREFOR

[75] Inventors: Shigeyuki Imamura; Hideo Misaki; Hidehiko Ishikawa; Kazuo Matsuura, all of Shizuoka, Japan

[73] Assignee: Toyo Jozo Kabushiki Kaisha, Shizuoka, Japan

[21] Appl. No.: 392,010

[22] Filed: Jun. 25, 1982

[30] Foreign Application Priority Data

Jun. 25, 1981 [JP] Japan ................................. 56-99314
Sep. 18, 1981 [JP] Japan ................................. 56-148313

[51] Int. Cl.$^3$ .......................... C12Q 1/00; C12Q 1/26; C12Q 1/32; C12Q 1/42; C12Q 1/44; C12Q 1/46; C12Q 1/48; C12Q 1/60; C12N 9/02; C12N 9/04; C12N 9/00; C12N 9/10; C12N 9/88; C12R 1/38

[52] U.S. Cl. .......................................... 435/4; 435/11; 435/15; 435/19; 435/20; 435/21; 435/25; 435/26; 435/189; 435/190; 435/183; 435/193; 435/232; 435/874

[58] Field of Search .................. 435/4, 11, 15, 18, 19, 435/20, 21, 25, 26, 28, 183, 189, 190, 193, 194, 198, 232, 253, 810, 817, 874

[56] References Cited

U.S. PATENT DOCUMENTS

| | | | |
|---|---|---|---|
| 3,901,763 | 8/1975 | Horiuchi et al. | 435/196 |
| 4,007,091 | 2/1977 | Nagasaki et al. | 435/11 |
| 4,071,413 | 1/1978 | Takahashi et al. | 435/4 |
| 4,141,792 | 2/1979 | Hayashi et al. | 435/19 |
| 4,168,203 | 9/1979 | Takahashi et al. | 435/21 |
| 4,195,126 | 3/1980 | Hall | 435/10 |
| 4,223,090 | 9/1980 | Mazza | 435/26 |
| 4,301,244 | 11/1981 | Kikuchi et al. | 435/4 |

OTHER PUBLICATIONS

Binstock et al., P.N.A.S. USA, 74(2):492–495 (1977).
Bergmeyer, *Method of Enzymatic Analysis*, Academic Press, New York, 832–837 (1974).
Binstock et al., *Methods in Enzymology*, vol. 71, Academic Press, New York, 403–411 (1981).
Schulz et al., *Methods in Enzymology*, vol. 71, Academic Press, New York, 398–403 (1981).
Pramanik et al., J. Bacteriol., 137(1):469–473 (1979).
Prawar et al., J. Biol. Chem., 256(8):3894–3899 (Apr. 25, 1981).

*Primary Examiner*—Esther M. Kepplinger
*Attorney, Agent, or Firm*—Young & Thompson

[57] ABSTRACT

An enzyme having enoyl-CoA hydratase activity, 3-hydroxyacyl-CoA dehydrogenase activity and 3-ketoacyl-CoA thiolase activity, all in the same enzyme, is produced by culturing the microorganism strain *Pseudomonas fragi* B-0771 FERM-P No. 5701, and isolating the enzyme thus produced from the culture medium. Such an enzyme is useful in an assay method for a fatty acid component in a sample, which fatty acid is originally present in the sample or is liberated from a fatty acid ester in the sample, comprising:

(a) converting the fatty acid to acyl-CoA;
(b) converting the thus-produced acyl-CoA to dehydroacyl-CoA;
(c) converting the thus-produced dehydroacyl-CoA to hydroxyacyl-CoA;
(d) converting the thus-produced hydroxyacyl-CoA to ketoacyl-CoA;
(e) converting the thus-produced ketoacyl-CoA to acyl-CoA; and measuring the detectable changes in the reaction mixture.

A composition suitable for such lipid assay comprises ATP or GTP,
CoASH,
NAD,
acyl-CoA synthetase activity,
acyl-CoA oxidase activity,
enoyl-CoA hydratase activity,
3-hydroxyacyl-CoA dehydrogenase activity, and
3-ketoacyl-CoA thiolase activity, wherein the last three activities are supplied by the new multi-active enzyme.

23 Claims, 5 Drawing Figures

ASSAY METHOD FOR LIPID COMPONENT, ASSAY COMPOSITION, AND PROCESS FOR PRODUCTION OF ENZYME USED THEREFOR

This invention relates to an assay method for a component in a sample, for example a free fatty acid, a free fatty acid liberated from a fatty acid ester, a fatty acid ester, or the enzyme activity which generates a free fatty acid from a fatty acid ester, and to a composition useful in practicing that method. The invention also relates to a process for the production of an enzyme having the activities of enoyl-CoA hydratase, 3-hydroxyacyl-CoA dehydrogenase and 3-ketoacyl-CoA thiolase in a single enzyme protein.

Hitherto-known enzymes for the β-oxidation of fatty acids and their enzyme actions are as follows:

[Reaction I: acyl-CoA synthetase, EC 6. 2. 1. 3]

[Reaction II: acyl-CoA dehydrogenase, EC 1. 3. 99. 3 (or acyl-CoA oxidase)]

[Reaction III: enoyl-CoA hydratase, EC 4. 2. 1. 17]

[Reaction IV: 3-hydroxyacyl-CoA dehydrogenase, EC 1. 1. 1. 35]

[Reaction V: 3-ketoacyl-CoA thiolase, EC 2. 3. 1. 16]

Heretofore, enzymatic assays for free fatty acids in serum specimens have been conducted as follows:

A specimen containing free fatty acid is treated with acyl-CoA synthetase in the presence of CoASH (coenzyme A) and ATP (adenosine triphosphate) to generate acyl-CoA, AMP (adenosine monophosphate) and pyrophosphate. The thus-produced AMP is treated with myokinase activity in the presence of ATP to form two moles of ADP (adenosine diphosphate) per mole of AMP. Then the thusformed ADP is treated with phosphoenolpyruvate in the presence of pyruvate kinase activity to form ATP and pyruvate which is treated with lactate dehydrogenase and reduced NAD (nicotine adenine dinucleotide) to liberate lactate and NAD, and the amount of reduced NAD consumed is measured by photometry with a decrease of optical density at 340 nm, two moles of reduced NAD being consumed per mole of fatty acid. [Analytical Biochemistry, 98, 341–345 (1979)].

Another method of assay for free fatty acid is known, in which free fatty acid is reacted with CoASH and ATP in the presence of acyl-CoA synthetase to form acyl-CoA, AMP and pyrophosphate. The formed acyl-CoA consumes oxygen in the presence of acyl-CoA oxidase to form 2,3-trans-enoyl-CoA and hydrogen peroxide. The thus-formed hydrogen peroxide is reacted with 4-aminoantipyrine, 2,4-dibromophenol and peroxidase to form a color-complex which is colorimetrically measured. [Anal. Biochem., 108, 6–10 (1980)].

These assay methods have a number of disadvantages. In a method using acyl-CoA oxidase activity, the formed hydrogen peroxide is reduced by CoASH and the second reaction step should be performed after changing the remaining CoASH of the first reaction step to a non-reductive substance with N-ethylmaleimide. Therefore, a simultaneous reaction is impossible. Another disadvantage is that lipase activity in serum is very weak, and hence the amount of free fatty acid liberated from fatty acid ester, as a substrate for lipase activity assay, is very small. These methods therefore cannot provide a sensitive assay method. In the first-mentioned assay method, the quantitative determination of the decreased amount of reduced NAD suffers from insufficient sensitivity.

We have found that the free fatty acid or the free fatty acid liberated from its ester in a sample can be advantageously assayed by a combination of processes comprising converting the fatty acid to acyl-CoA, which is converted to dehydroacyl-CoA, converting the dehydroacyl-CoA to hydroxyacyl-CoA, transforming the hydroxyacyl-CoA to ketoacyl-CoA, and converting the ketoacyl-CoA to acyl-CoA.

The acyl-CoA produced in the final reaction step has an acyl group which is two carbon atoms shorter than the fatty acid in the sample. The said acyl-CoA is also decomposed to dehydroacyl-CoA, hydroxyacyl-CoA and ketoacyl-CoA to form a fatty acid which is two carbon atoms shorter than the original.

In this assay method, the fatty acid in the sample is decomposed as follows:

(a) acyl-CoA is formed by the action of acyl-CoA synthetase activity in the presence of ATP or GTP and CoASH;

(b) acyl-CoA is changed to dehydrocacyl-CoA by acyl-CoA oxidase activity and oxygen;

(c) dehydroacyl-CoA is changed to hydroxyacyl-CoA by enoyl-CoA hydratase activity and water;

(d) hydroxyacyl-CoA is transformed to ketoacyl-CoA by NAD and 3-hydroxyacyl-CoA dehydrogenase activity; and (e) ketoacyl-CoA is transformed to two-carbon-atomless acyl-CoA by CoASH and 3-ketoacyl-CoA thiolase. The thus-produced acyl-CoA is again decomposed via β-oxdation whereupon the detectable changes in the cycle are detected.

We have also found that a bacterial strain belonging to genus Pseudomonas, isolated from a soil sample collected from a pear field in Sudama-cho, Kitakoma-gun, Yamanashi-ken, Japan, produces an enzyme, having the multiple enzyme activities of enoyl-CoA hydratase of reaction III hereinbefore, 3-hydroxyacyl-CoA dehydrogenase of reaction IV hereinbefore and 3-ketoacyl-CoA thiolase of reaction V hereinbefore, in a single enzyme protein (hereinafter designated as multi-active enzyme), and that the said multi-active enzyme can be used for the assay of fatty acid.

The strain is referred to as *Pseudomonas fragi* B-0771 and has been deposited in the Fermentation Institute, Agency of Industrial Technology & Sciences, M.I.T.I., Japan as its permanent culture collection number FERM-P No. 5701.

The strain B-0771 has the following taxonomical properties:

(A) Macroscopic observation:
(1) Nutrient agar plate: Colonies convex, round, smooth edges, semi-lustrous, grayish white to pale yellow. No soluble pigment formation.
(2) Nutrient agar slant: Linearly good growth. Semi-lustrous, grayish white to pale yellow. No soluble pigment formation.
(3) Liquid culture: Homogeneously turbid, precipitation. No formation of capsules.

(B) Microscopic observation:
Straight or slightly curved bacilli. Single or double, sometimes long chains. 0.4–0.6×0.5–3.0 μm. Motile with polar flagella. No spore formation.

(C) Physiological and biochemical characteristics:

| | |
|---|---|
| Gram's stain | − |
| O.F. test | O |
| Catalase | + |
| Oxidase | + |
| Lecithinase | − |
| Urease SSR medium | − |
| Christensen medium | + |
| Gelatin hydrolysis | − |
| Starch hydrolysis | − |
| Casein hydrolysis | − |
| Esculin hydrolysis | − |
| Arginine hydrolysis | + |
| Poly-β-hydroxybutyrate (PHB) accumulation | − |
| Indole formation | − |
| Hydrogen sulfate formation | − |
| Acetoin formation | − |
| MR test | − |
| Nitrate reduction | − |
| Citrate utilization | + |

Acid formation from sugar:
Acid formation, no gas formation: L(+)arabinose, cellobiose, fructose, fucose, galactose, glucose, glycerin, lactose, maltose, mannose, melibiose, rhamnose, sucrose, trehalose, xylose.
No acid formation, no gas formation: adnitol, dulcitol, meso-erythritol, inositol, inulin, mannitol, melezitose, raffinose, salicin, sorbose, sorbitol, starch.

As hereinabove explained, the strain B-0771, having the properties of Gram negative, motile with polar flagella, catalase and oxidase positive, aerobic nature of oxidative decomposition of glucose, is recognized as a microorganism belonging to genus Pseudomonas.

Referring to the description of *Pseudomonas fragi* in J. Gen. Microbiol., 25, 379–408 (1961), the strains are identical with each other as follows:

| | The strain B-0771 | *Pseudomonas fragi* |
|---|---|---|
| Arginine decomposition | + | + |
| PHB accumulation | − | − |
| Gelatin liquefaction | − | − |
| Starch hydrolysis | − | − |
| Casein hydrolysis | − | − |
| Esculin decomposition | − | − |
| Indole formation | − | − |
| H₂S formation | − | − |
| Acetoin formation | − | − |
| Nitrate reduction | − | d |
| Citrate utilization | + | + |

Furthermore, comparative studies of the strain B-0771 and type culture *Pseudomonas fragi* ATCC 4973 have been carried out. The results are shown in Table 1.

TABLE 1

| | Strain B-0771 | *Pseudomonas fragi* ATCC 4973 |
|---|---|---|
| Gram's stain | − | − |
| Motile | + | + |
| Flagella | polar | polar |
| O.F. Test | O | O |
| Catalase | + | + |
| Oxidase | + | + |
| Urease | | |
| SSR | − | − |
| Christensen | (+) | (+) |
| Arginine decomposition | + | |
| Starch hydrolysis | − | − |
| Gelatin liquefaction | − | − |
| Casein hydrolysis | − | − |
| Esculin decomposition | − | − |
| Indole formation | − | − |
| H₂S formation | − | − |
| Acetoin formation | − | − |
| Nitrate reduction | − | − |
| Citrate utilization | + | + |
| Acid formation from sugar | | |
| adonitol | − | − |
| L(+)arabinose | + | + |
| cellobiose | + | + |
| dulcitol | − | − |
| mesoerythritol | − | − |
| fructose | + | + |
| fucose | + | + |
| galactose | + | + |
| glucose | + | + |
| glycerin | (+) | + |
| inositol | − | − |
| inulin | − | − |
| lactose | + | + |
| maltose | + | + |
| mannitol | − | − |
| mannose | + | + |
| melezitose | − | − |
| melibiose | + | + |
| raffinose | − | − |
| L(+)rhamnose | (+) | + |
| salicin | − | − |
| L-sorbose | − | − |
| starch | − | − |
| sucrose | + | + |
| trehalose | + | + |
| xylose | + | + |

As shown in the above table, the strain B-0771 has similar taxonomical properties to those of the type culture strain *Pseudomonas fragi* ATCC 4973.

An object of the present invention is to provide an assay method for a component in a sample, comprising the following steps:
(a) converting fatty acid to acyl-CoA;
(b) converting acyl-CoA to dehydroacyl-CoA;
(c) converting dehydroacyl-CoA to hydroxyacyl-CoA;

(d) converting hydroxyacyl-CoA to ketoacyl-CoA;
(e) converting ketoacyl-CoA to acyl-CoA; and
detecting the detectable changes.

Another object of the present invention is to provide a composition for assay comprising at least the following:
ATP or GTP;
CoASH;
NAD;
acyl-CoA synthetase;
acyl-CoA oxidase;
enoyl-CoA hydratase;
3-hydroxyacyl-CoA dehydrogenase; and
3-detoacyl-CoA thiolase.

A further object of the present invention is to provide a process for the production of multi-active enzyme which comprises culturing a multi-active-enzyme-producing microorganism belonging to genus Pseudomonas, and isolating the thus-produced enzyme from the culture medium.

These and other objects, features and advantages of the present invention will become apparent from a consideration of the following description, taken in connection with the accompanying drawings, in which.

The samples to be assayed according to the present invention contain fatty acid. Examples of the fatty acid are caproic acid, caprylic acid, capric acid, lauric acid, myristic acid, palmitic acid, palmitoleic acid, stearic acid, oleic acid, linolic acid or linolenic acid.

Further examples of fatty acids to be analyzed are free fatty acids or fatty acid esters as components in dairy products such as butter, margarine, cheese, ham, milk or mayonnaise; free fatty acids or fatty acid esters in specimens such as blood and urine; the reaction products of enzymatic action thereon; free fatty acids or their salts and fatty acid esters as components in drug preparation; or fatty acids as substrates for commercial enzyme reagents or liberated fatty acids from the action of commercial enzyme reagents.

Fatty acid can be liberated from a fatty acid ester by alkaline saponification using sodium hydroxide or potassium hydroxide, or by enzymatic action.

In the combination of fatty acid ester and enzymatic activity thereon to generate fatty acid, fatty acid ester can be assayed after generating the fatty acid, and the enzymatic activity can also be assayed by assaying liberated fatty acid from the sample containing fatty acid ester. This combination, however, is not to be construed as limitative, and any combination which liberates fatty acid can be included.

When the fatty acid ester is a glyceride such as a monoglyceride, diglyceride or triglyceride, and the enzymatic activity is lipase activity, glyceride or lipase activity can be assayed by determining fatty acid liberated from the glyceride.

These assays are used for triglyceride assay in serum and pancreatic lipase assay in serum. In the latter case, turbidity of the reaction system can be prevented preferably by using a mono- or diglyceride and adding albumin such as bovine albumin.

A combination system of fatty acid ester and enzyme which acts on the said fatty acid ester is as exemplified as follows:

| Fatty acid ester | Enzyme activity: |
|---|---|
| lecithin | phospholipase $A_1$, phospholipase $A_2$ or phospholipase B |
| lysolecithin | lysophospholipase |
| phosphatidate | phosphatidate phosphatase and lipase |
| lecithin | phospholipase C and lipase |
| lecithin | phospholipase D, phosphatidate phosphatase and lipase |
| acylcholine | choline esterase |
| cholesterol ester | cholesterol esterase |
| lecithin and cholesterol | lecithin cholesterol acyltransferase, cholesterol esterase or lysophospholipase. |

Fatty-acid-related components such as the substrates and enzymes hereinabove can be assayed by assaying fatty acid. In the systems which liberate fatty acid, the amounts of reagents used are selected according to reaction conditions, so as to carry the liberation of fatty acid to completion. The reaction temperature for liberating fatty acid is usually approximately 37° C., and the reaction time should naturally be a sufficient time for completely liberating fatty acid, and is more than one minute.

Embodiments of the reaction steps (a), (b), (c), (d) and (e) hereinbefore are given as follows:

(a) Reaction which changes fatty acid to acyl-CoA:

For example, a reaction using acyl-CoA synthetase activity, which catalyzes the reaction of fatty acid, ATP and CoASH to Acyl-CoA, AMP and pyrophosphate (PPi), ATP and CoASH can be illustrated as follows:

R—CH$_2$—CH$_2$—COOH + ATP +

(fatty acid)

(acyl-CoA)

(b) Reaction which changes acyl-CoA to dehydroacyl-CoA:

For example, a reaction using acyl-CoA oxidase activity, which catalyzes the reaction of acyl-CoA and oxygen to dehydroacyl-CoA and hydrogen peroxide, and oxygen, can be illustrated as follows:

(acyl-CoA)

-continued (dehydroacyl-CoA)

(c) Reaction which changes dehydroacyl-CoA to hydroxyacyl-CoA:

For example, a reaction of enoyl-CoA hydratase activity, which catalyzes the reaction of dehydroacyl-CoA to hydroxyacyl-CoA in the presence of water, and water can be illustrated as follows:

(hydroxyacyl-CoA)

(d) Reaction which changes hydroxyacyl-CoA to ketoacyl-CoA:

For example, a reaction using 3-hydroxyacyl-CoA dehydrogenase, which catalyzes the reaction of hydroxyacyl-CoA and NAD to ketoacyl-CoA and reduced NAD, and NAD can be illustrated as follows:

(e) Reaction which changes ketoacyl-CoA to acyl-CoA:

For example, a reaction using 3-ketoacyl-CoA-CoA-thiolase, which catalyzes the reaction of ketoacyl-CoA to acyl-CoA and acethyl-CoA in the presence of CoASH, and CoASH can be illustrated as follows:

(acyl-CoA)

The enzyme used in the above processes can be any of the enzymes originating from animals or microorganisms. Commercially available enzymes and isolated enzymes from any source can be used.

Other sources of acyl-CoA synthetase are as follows:
Guinea-pig liver [J. Biol. Chem., 204, 329 (1953)];
Rat, mouse, bovine, porcine liver (Jap. Pat. Unexam. Publ. No. 55-74791);
Escherichia coli [Eur. J. Biochem., 12, 576 (1970)];
Bacillus megaterium [Biochem., 4(1), 85 (1965)];
Aerobactoer aerogenes IFO 3318, Seratia marcescens IFO 3052,
Proteus mirabilis IFO 3849, Staphylococcus aureus IFO 3060,
Pseudomonas aeruginosa IFO 3919, Fusarium oxysporum IFO 5942,
Gibberella fujikuroi IFO 6604 and Candida lipolytica IFO 0717 [J. Bacteriol., 105(3), 1216 (1971), ibid., 114(1), 249 (1973), Jap. Pat. Unexam. Publ., No. 55-74790, ibid., No. 55-99187].

Another embodiment of acyl-CoA synthetase is an enzyme which catalyzes a reaction from fatty acid, GTP and CoASH to acyl-CoA, GDP and orthophosphate. [bovine liver, J. Biol. Chem., 239(6), 1694 (1964)].

Examples of sources of acyl-CoA oxidase are:
rat liver [Biochem. Biophys. Res. Comm., 83(2), 479 (1978)];
Candida utilis, Candida lipolytica IFO 1548, Candida tropicalis IFO 0589, Saccharomyces cerevisiae IFO 0213, Saccharomyces cerevisiae Y0036 FERM-P No. 5174 (DSM 2138) [Jap. Pat. Unexam. Publ. No. 56-61991];
Eupenicillium javanicum IFO 7992, Monascus sp. M-4800 FERM-P No. 5225 (DSM 2136) [ibid., No. 56-61991];
Aspergillus candidus M-4815 FERM-P No. 5226 (DSM 2135) [ibid., No. 56-61991]; Arthrobacter sp. B-0720 FERM-P No. 5224 (DSM 2137) (ibid., No. 51-61991); Macrophomina phaseoli ATCC 14383, Cladosporium resinae IFO 6367 [Arch. Biochem. Biophys., 176, 591 (1976), Jap. Pat. Unexam. Publ. No. 55-118391, ibid., No. 56-8683, ibid., No. 56-61991].

The above acyl-CoA oxidase can be replaced by acyl-CoA dehydrogenase [EC 1. 3. 99. 3, acyl-CoA: (acceptor) oxidoreductase]This enzyme can be obtained from, for example, porcine, bovine and sheep liver [J. Biol. Chem., 218, 717 (1956), ibid., 218, 701 (1956), J. Am. Chem. Soc., 75, 2787 (1953), Biochim Biophys. Acta, 22, 475 (1956)].

In the reaction of acyl-CoA to produce dehydroacyl-CoA, an electron acceptor, for example, 2,6-dichlorophenol indophenol, 2-(p-iodo-phenyl)-3-(p-nitrophenyl)-5-phenyl-2H-tetrazolium chloride (INT), 3-(4,5-dimethyl)-2-thiazolyl-2,5-diphenyl-2H-tetrazolium bromide (MTT), 3,3'-(4,4'-biphenylene)-bis(2,5-diphenyl-2H-tetrazolium chloride) (neo-TB), 3,3'-(3,3'-dimethoxy-4,4'-biphenylene)-bis-[2-(p-nitrophenyl)-5-phenyl-2H-tetrazolium chloride] (NTB), 3,3'-(3,3'-dimethoxy-4,4'-bis[2,5-bis(p-nitrophenyl)-2H-tetrazolium chloride] (TNTB) or 3,3'-(3,3'-dimethoxy-4,4'-biphenylene)-bis-(2,5-diphenyl-2H-tetrazolium chloride) (TB), is used with phenazine methosulfate.

Furthermore, enzymes showing enoyl-CoA hydratase activity, 3-hydroxyacyl-CoA dehydrogenase activity and 3-ketoacyl-CoA thiolase activity can preferably be isolated from animal tissues containing them. [J. Biol. Chem., 218, 971 (1956), ibid., 207, (1954), ibid, 208, 345 (1954), Angew. Chem., 64, 687 (1952), and Biochim. Biophys. Acta, 26, 448 (1957).]

Multi-active enzyme comprising enoyl-CoA hydratase activity, 3-hydroxyacyl-CoA dehydrogenase activity and 3-ketoacyl-CoA thiolase activity in a single enzyme protein is preferably used. Examples of the said enzyme-producing microorganisms are Escherichia coli [Proc. Natl. Acad. Sci., 74(2), 492 (1977)] and the above-identified Pseudomonas fragi B-0771 FERM-P No. 5701.

The enzyme obtained from Pseudomonas fragi B-0771 FERM-P No. 5701 has the following properties:
(1) Assay method of enzyme activity:

(a) Assay method of enoyl-CoA hydratase activity:

| | |
|---|---|
| 0.2 M Tris-HCl buffer (pH 9.0) | 0.4 ml |
| 1 M KCl | 0.1 ml |
| 40 mM NAD | 0.1 ml |
| 15 mM palmitenoyl-CoA | 0.1 ml |
| 1% bovine serum albumin | 0.05 ml |
| 0.25% nitrotetrazolium blue | 0.1 ml |
| 125 U/ml 3-hydroxyacyl-CoA dehydrogenase (Boehringer) | 0.01 ml |
| distilled water | 0.14 ml |
| Total | 1.00 ml |

The above reaction mixture was preincubated at 37° C. for 2 minutes, and the enzyme solution was added therein, then the mixture was incubated at 37° C. for 10 minutes. 0.5% sodium dodecyl sulfate (2.0 ml) was added to stop the reaction and the optical density (absorption at $\Delta A_{550}$) was measured at a wavelength of 550 nm.

One unit (1 U) of enzyme is defined as the amount of enzyme which generates 1 μmole of reduced NAD in one minute.

Enzyme activity is defined by the following equation:

$$\text{Enzyme activity (U/ml)} = \Delta A_{550} \times \frac{1}{4} \times \frac{1000}{50} \times \frac{1}{10}$$

(b) Assay method of 3-hydroxyacyl-CoA dehydrogenase activity:

| | |
|---|---|
| 0.2 M Tris HCl buffer (pH 8.5) | 0.5 ml |
| 1 M KCl | 0.05 ml |
| 40 mM NAD | 0.1 ml |
| 15 mM 3-hydroxypalmitoyl-CoA | 0.1 ml |
| 1% bovine serum albumin | 0.05 ml |
| 0.25% nitrotetrazolium blue | 0.1 ml |
| 30 U/ml diaporase | 0.1 ml |
| Total | 1.00 ml |

The enzyme solution (50 μl) was added to the above reaction mixture, which was preincubated at 27° C. for 2 minutes, and the mixture was incubated at 37° C. for 10 minutes. 0.5% sodium dodecyl sulfate (2.0 ml) was added to stop the reaction and the absorbency was measured at 550 nm ($\Delta A_{550}$) One unit (1 U) is defined as the amount of enzyme which generates 1 μmole of reduced NAD in one minute. Enzyme activity is defined by the following equation:

$$\text{Enzyme activity (U/ml)} = \Delta A_{550} \times \frac{1}{4} \times \frac{1000}{50} \times \frac{1}{10}$$

(c) Assay method of 3-ketoacyl-CoA thiolase activity:

| | |
|---|---|
| 0.2 M Tris-HCl buffer (pH 8.0) | 0.2 ml |
| 10 mM CoASH | 0.05 ml |
| 0.2 mM 3-ketopalmitoyl-CoA | 0.1 ml |
| 100 mM MgCl$_2$ | 0.1 ml |
| 1 mM dithiothreitol | 0.1 ml |
| distilled water | 0.45 ml |
| Total | 1.00 ml |

To the reaction mixture in a 1 ml quartz cell at 37° C. was added enzyme solution in the amount of 20 μl, and the mixture was incubated at 37° C. The decreasing amount of 3-ketopalmitoyl-CoA consumed during the reaction was measured at equal time intervals by changes of optical density (absorbency) at 303 nm ($OD_{303}$). One unit (1 U) is defined as the amount of enzyme which consumes 1 μmole of 3-ketopalmitoyl-CoA in one minute. Enzyme activity is defined in the following equation:

$$\text{Enzyme activity (U/ml)} = (OD_{303}/\text{min.}) \times \frac{1}{13.5} \times \frac{1000}{20}$$

(2) Enzyme action:

The following enzyme activities have been observed:

Enoyl-CoA hydratase: catalyzes a reaction which forms 1 mole of hydroxyaceyl-CoA from 1 mole of dehydroacyl-CoA and 1 mole of water.

3-hydroxyacyl-CoA dehydrogenase: catalyzes a reaction which forms 1 mole of ketoacyl-CoA and 1 mole of reduced NAD from 1 mole of hydroxyacyl-CoA and 1 mole of NAD.

3-ketoacyl-CoA thiolase: catalyzes a reaction which forms 1 mole of acyl-CoA and 1 mole of acetyl-CoA from 1 mole of ketoacyl-CoA and 1 mole of CoASH.

(3) Evidence of but a single enzyme protein:

Crude enzyme was prepared from microbial cells of *Pseudomonas fragi* B-0771 and purified by several purification procedures. Each enzyme activity was measured according to the assay methods hereinabove. The results are shown in the following Table 2:

TABLE 2

| | Enoyl-CoA hydratase activity (U/mg) | 3-hydroxyacyl-CoA dehydrogenase activity (U/mg) | 3-ketoacyl-CoA thiolase activity (U/mg) |
|---|---|---|---|
| Crude enzyme | 36.1 | 18.2 | 15.1 |
| DEAE-cellulose CL-6B column | 58.9 | 30.0 | 24.5 |
| Hydroxyapatite gel column | 210.3 | 105.0 | 85.6 |
| Tyopeal HW-60 column | 216.5 | 110.0 | 90.2 |

Each enzyme activity exactly corresponds to the activity at each purification step and these three enzyme activities remain in the same protein. Therefore the said three enzyme activities are embodied in a single enzyme protein.

Furthermore, purified enzyme (2.0 mg) obtained in the example hereinbelow (purified by Toypeal HW-60 column chromatography) was disposed in an isoelectric focusing electrophoresis device using carrier ampholyte, and each enzyme activity was measured. Three enzyme activities were observed in a single peak in a fraction at pH 4.9.

(4) Substrate specificity:

3-hydroxyacyl-CoA dehydrogenase activity was measured by using the following embodiments of 3-hydroxyacyl-CoA:

| Substrate | Relative activity (%) |
|---|---|
| 3-hydroxycaproyl-CoA | 56.5 |
| 3-hydroxycaprylyl-CoA | 88.1 |
| 3-hydroxycapryl-CoA | 99.0 |
| 3-hydroxylauryl-CoA | 100.0 |
| 3-hydroxymyristoyl-CoA | 98.0 |
| 3-hydroxypalmitoyl-CoA | 75.5 |
| 3-hydroxystearyl-CoA | 30.5 |
| 3-hydroxyarachidoyl-CoA | 9.5 |
| 3-hydroxyoleyl-CoA | 57.5 |

| Substrate | Relative activity (%) |
| --- | --- |
| 3-hydroxylinolenyl-CoA | 99.0 |

The enzyme has also substrate specificity at least as to palmitoenoyl-CoA and 3-ketopalmitoyl-CoA.

Figure 1:
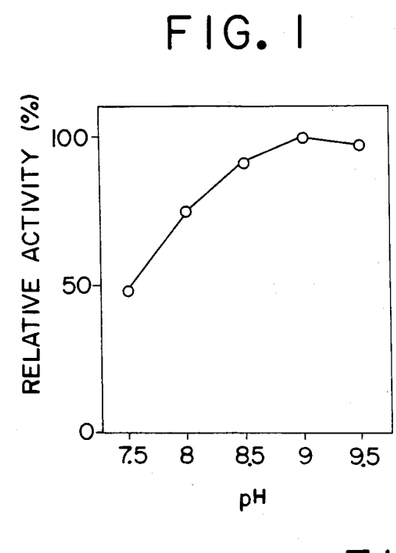
FIG. 1 is a graph of the optimum pH of the 3-hydroxyacyl-CoA dehydrogenase activity in the multi-active enzyme prepared from *Pseudomonas fragi* B-0771 FERM-P No. 5701.

(5) Optimum pH:

3-hydroxypalmitoyl-CoA was used as a substrate. 3-hydroxyacyl-CoA activity was measured using Tris-HCl buffer at pH 7.5–9.5. The results are shown in FIG. 1. The optimum pH is approximately at pH 9.

Figure 2:
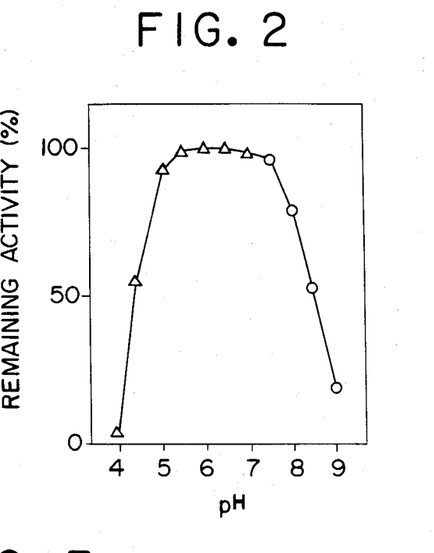
FIG. 2 is a graph of the pH-stability of the 3-hydroxyacyl-CoA dehydrogenase activity in the multi-active enzyme.

(6) pH-stability:

Enzyme solution (5 U/ml) dissolved in various 10 mM buffer solutios (pH 4–7: dimethylglutarate-NaOH buffer, pH 7.5–9: Tris-HCl buffer) was incubated at 37° C. for 60 minutes, and the remaining activity was measured according to an assay method for 3-hydroxyacyl-CoA dehydrogenase activity. The results are shown in FIG. 2, in which the enzyme is seen to be stable at pH 5–8.

Figure 3:
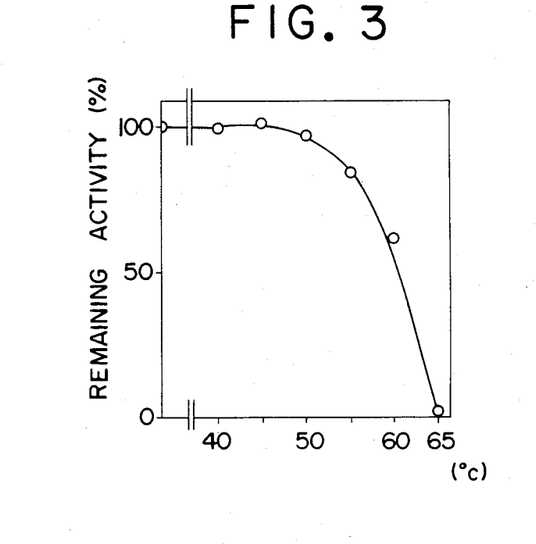
FIG. 3 is a graph of the heat-stability of the 3-hydroxyacyl-CoA dehydrogenase activity in the multi-active enzyme.

(7) Heat stability:

Enzyme solution (15 U/ml) dissolved in 10 mM dimethylglutarate-NaOH buffer (pH 7.0) was incubated at various temperatures for 10 minutes and the remaining activity was measured according to an assay method for 3-hydroxyacyl-CoA dehydrogenase activity.

The results are shown in FIG. 3, in which it is seen that the enzyme is stable up to approximately 50° C.

(8) Isoelectric point:

Isoelectric focusing using carrier ampholyte was used for measuring the isoelectric point of the enzyme, whereby it was found that the isoelectric point is pH 4.9.

(9) Effect of metal ions:

The effect of metal ions was measured on 3-hydroxyacyl-CoA dehydrogenase activity.

| Metal ion | Relative activity (%) |
| --- | --- |
| Control | 100 |
| 1 mM $CaCl_2$ | 113 |
| 1 mM $MgCl_2$ | 113 |
| 1 mM $MnCl_2$ | 32 |
| 1 mM $ZnCl_2$ | 25 |
| 1 mM $CuCl_2$ | 12 |
| 1 mM $BaCl_2$ | 106 |
| 1 mM $NiCl_2$ | 95 |
| 1 mM $CoCl_2$ | 34 |

(10) Effect of surface active agents:

The effect of surface active agents was measured on 3-hydroxyacyl-CoA dehydrogenase activity.

| Surface active agent | Relative activity (%) |
| --- | --- |
| Control | 100 |
| 0.1% Triton X-100 | 96 |
| 0.1% Adekatol SO-145 | 81 |
| 0.1% laurylbenzene sulfonate | 0 |
| 0.1% sodium lauryl sulfate | 0 |
| 0.1% sodium deoxycholate | 2 |
| 0.1% cetyltrimethylammonium chloride | 0 |
| 0.1% cetylpyridinium chloride | 0 |

As explained above, the multi-active enzyme of the present invention has enoyl-CoA hydratase activity, 3-hydroxyacyl-CoA dehydrogenase activity and 3-ketoacyl-CoA thiolase activity in a single enzyme protein.

Embodiments of processes for the production of the multi-active enzyme can be as follows:

The microorganisms used for the production of the multi-active enzyme are not limited to the above-mentioned *Pseudomonas fragi* B-0771 FERM-P No. 5701, as other strains belonging to genus Pseudomonas which produce the multi-active enzyme can also be used in the present invention.

In a preferred embodiment, multi-active-enzyme-producing microorganisms belonging to Pseudomonas are cultured in a conventional medium for enzyme production. Solid or liquid culture can be used for fermentation; however, submerged aeration culture is preferable for industrial production.

The nutrient sources which are used for conventional microorganism cultivation can be used. Assimilable carbon sources such as glucose, sucrose, lactose, starch, maltose, dextrin, molasses and glycerin can be used. Assimilable nitrogen sources such as corn steep liquor, soybean powder, cotton seed oil, wheat gluten, peptone, meat extract, yeast extract, yeast powder and casein hydrolysate can also be used. Salts such as the phosphate, sulfate or other salt of magnesium, clacium, potassium, sodium, zinc, iron and manganese can be used if required. In order to increase the production of the multi-active enzyme, fatty acids of $C_{8-20}$ such as oleic acid, palmitic acid and stearic acid can be added to the medium.

The cultivation temperature can be varied for growing the microorganisms and producing the enzyme, and is 26°–32° C., preferably 30° C. The cultivation time depends on the conditions employed and is usually 10–40 hours. Cultivation should naturally be terminated when the maximum enzyme activity is obtained.

The thus-produced multi-active enzyme is contained in the cells of the cultured microorganisms.

Isolation of the enzyme can be performed as follows:

First, the cultured cells are collected by filtration or centrifugation. The cells are disrupted by means of sonication, a French press, glass beads treatment or lysozyme treatment, wherein surface active agents such as Triton X-100 (trade name) or Adekatol SO-145 (trade name) can optionally be added.

The enzyme is precipitated by adding a water-miscible organic solvent such as methanol, ethanol or acetone, and by salting out by adding e.g. ammonium chloride. The precipitated crude enzyme is purified by dissolving the crude enzyme, dialyzed with a cellophane tube, chromatographed using DEAE-cellulose, DEAE-Sepharose, CM-Sephadex or an ion exchange resin, and gelfiltrated with Sephadex G-200, Sephalose CL-6B, Sephacryl S-200 or Toyopeal HW-60. The obtained enzyme is lyophilized to obtain the purified multi-active enzyme.

The amount of enzyme used in each enzymatic process can be a sufficient amount for enzyme reaction, and is varied depending on the amount and number of carbons in the fatty acid in the specimen, and hence is not limited. For example, in the case wherein a specimen which contains 0.005–0.05 μmole of $C_{18}$ oleic acid is reacted at 37° C. for 5–10 minutes, acyl-CoA synthetase activity is generally more than 1 U, preferably 5–15 U, and the multi-active enzyme of the present invention is usually more than 0.1 U, preferably 1–25 U.

The amount of reagents in the reaction steps, for example, ATP or GTP and CoASH in step (a), NAD in step (d) and CoASH in step (3), should be sufficient for the amount of fatty acid in the sample and the number of β-oxidation cycles depending on the number of carbon atoms in the said fatty acid. For example, in the case of 0.01 μmole of oleic acid, the amount of ATP or GTP is more than 0.1 μmole, preferably more than 0.5 μmole; the amount of CoASH is more than 0.1 μmole, preferably more than 0.5 μmole; and the amount of NAD is more than 0.1 μmole, preferably more than 0.5 μmole.

In reaction step (b), the enzymatic action of acyl-CoA oxidase is exerted with dissolved oxygen in a sample, and in step (c), water in the sample can be used.

A water-soluble magnesium salt such as magnesium chloride which generates magnesium ions can be used for the acyl-CoA synthetase reaction. In reaction step (b), hydrogen peroxide generated by the action of acyl-CoA oxidase is preferably removed by catalase action.

Components for assay use, which contain at least ATP or GTP and CoASH, NAD, acyl-CoA synthetase activity, acyl-CoA oxidase activity, enoyl-CoA hydratase activity, 3-hydroxyacyl-CoA dehydrogenase activity and 3-ketoacyl-CoA thiolase activity, can be prepared.

In the present invention, the multi-active enzyme hereinbefore is preferably used. As explained above, a water-soluble magnesium salt, catalase and a non-ionic surface active agent, such as Triton X-100 (trade name), are added as the components. The solution is prepared by adding neutral to weak alkaline water or a buffer. Furthermore, in the case of assay for fatty acid ester, fatty acid liberating agents such as enzymes are added to the components, or alternatively, in the case of assay for the activity of an enzyme on a fatty acid ester, the fatty acid ester is previously added to the components. For example, for lipase activity assay components, a glyceride, preferably a monoglyceride or diglyceride, is added to the components for assay hereinbefore. Albumin is preferably added thereto. For triglyceride assay components, for example, lipase is added thereto.

Further embodiments of the components for assay are as follows:

Components for the assay of phospholipase $A_1$ activity, phospholipase $A_2$ activity and phospholipase B activity which comprises lecithin as a fatty acid ester;

Components for the assay of lysophospholipase activity which contain lysolecithin as a fatty acid ester;

Components for the assay of phosphatase activity which contain phosphatidate as a fatty acid ester and lipase activity;

Components for the assay of phospholipase C activity which contain lecithin as a fatty acid and lipase activity;

Components for the assay of phospholipase D activity which contain lecithin as a fatty acid, phosphatidate phosphatase activity and lipase activity;

Components for the assay of choline esterase activity which contain acylcholine as a fatty acid ester;

Components for the assay of cholesterol esterase activity which contain a sterol ester as a fatty acid ester;

Components for the assay of lecithin which contain phospholipase $A_1$ activity, phospholipase $A_2$ activity, phospholipase B activity, phospholipase C activity and lipase activity, or phospholipase D activity and phosphatidate phosphatase activity and lipase activity;

Components for the assay of lysolecithin which contain lysophospholipase activity;

Components for the assay of cholesterol ester which contain cholesterol esterase activity;

Components for assay of lecithin-cholesterol-acyltransferase activity which contain a fatty acid ester of cholesterol and lecithin, and cholesterol esterase activity or lysophospholipase activity; and Components for the assay of cholesterol which contain lecithin as a fatty acid ester, lecithin cholesterol acyl transferase activity and cholesterol esterase activity or lysophospholipase activity.

Fatty acid in a sample can be assayed by using the components for assay hereinabove. The amount of the sample is generally more than 5 μl and is mixed with more than 1 ml of the solution of components for assay. The assay is conventionally performed at 37° C. The incubation time is usually more than one minute. Preferably 5–10 minutes; and as long a time as possible is preferred, for higher sensitivity.

The assay medium is preferably a buffer solution within the stable pH range of the enzymes, and is usually a weakly acidic or alkaline solution such as water, a phosphate buffer of pH 6.5–8, a Tris-HCl buffer, an imidazol-HCl buffer, a dimethyglutarate-NaOH buffer of a Pipes-NaOH buffer.

After incubation, detectable changes in the reaction mixture are detected. The said detectable changes mean that at least one mole of the components has been consumed or generated in one cycle of β-oxidation.

Most conventionally, changes in the amount of reduced NAD from NAD in the reaction are determined. The detection means for reduced NAD measure the specific absorbency of reduced NAD. NAD has a maximum absorption at 260 nm, whereas reduced NAD has a maximum absorption at 260 and 340 nm, and hence an absorbency of 320–360 nm, preferably of 340 nm, is used.

Further determination of reduced NAD is by a colorimetric assay method based on the coloration of the electron transfer system as an electron acceptor for reduced NAD. Embodiments of the coloration reagent of the electron transfer system are electron acceptors, for example a water-soluble tetrazolium salt such as INT, MTT, Neo-TB, NTB, TNTB and TB, and these are preferably used with diaphorase and phenazinemethosulfate for the improvement of electron transport. The electron transfer reagent can be previously added to the components for assay hereinbefore, or can be added after the reaction.

The reduced NAD formed in the reaction is reacted with the electron transfer reagents to produce color changes which can be measured by their absorption wavelengths.

A further embodiment for the assay of reduced NAD is by using an enzyme such as reduced NAD oxidase. The said enzyme, for which reduced NAD is the substrate, is preferably immobilized by any of the prior known conventional immobilizing techniques.

The said immobilized enzyme is assembled in the oxygen-electrode to prepare a reduced NAD oxidase electrode.

The amount of consumed oxygen from reduced NAD, generated during the reaction, can be measured electrically.

The amount of fatty acid can be determined based on the amount of reduced NAD thus formed. Or the amount of fatty acid ester or enzyme activity in a sample can be measured by the said amount of fatty acid.

The consumed reagent such as CoASH or generated acyl-CoA can also be assayed as the detectable change.

The assay method and components for assay of the present invention hereinabove are simple to use and of high sensitivity, and can be, for example, applied for lipase activity assay in clinical diagnoses of pancreatic function.

Assay methods for acyl-CoA synthetase and acyl-CoA oxidase used in the present invention are as follows:

(1) Assay method for acyl-CoA synthetase activity:
(I) Reaction mixture I:

| | |
|---|---|
| 0.2 M phosphate buffer (pH 7.5) | 0.2 ml |
| 10 mM ATP | 0.1 ml |
| 10 mM MgCl$_2$ | 0.1 ml |
| 10 mM CoASH | 0.05 ml |
| 5% Triton X-100 containing 1 mM palmitic acid solution | 0.2 ml |
| distilled water | 0.35 ml |
| Total | 1.00 ml |

(II) Reaction mixture II:

| | |
|---|---|
| 0.2 M phosphate buffer (pH 7.5) | 0.5 ml |
| 20 mM N—ethylmaleimide | 0.1 ml |
| 15 mM 4-aminoantipyrine | 0.3 ml |
| 0.3% 3-methyl-N—ethyl-N—($\beta$-hydroxyethyl) ($\beta$-hydroxyethyl) aniline | 0.25 ml |
| peroxidase (100 PPU/ml) | 0.1 ml |
| 0.5% sodium azide | 0.1 ml |
| acyl-CoA oxidase (120 U/ml) | 0.1 ml |
| distilled water | 0.55 ml |
| Total | 2.00 ml |

An enzyme solution (50 $\mu$l) is added to the reaction mixture I and the mixture is incubated at 37° C. for 10 minutes. The reaction mixture II is added thereto, and the mixture is incubated at 37° C. for 5 minutes and the absorbency at 550 nm ($\Delta A_{550}$) is measured.

Enzyme activity is defined by the following equation:

$$\text{Enzyme activity (U/mg)} = \frac{\Delta A_{550}/10}{32.0 \times \frac{1}{2}} \times \frac{3.05}{0.05} \times C^*$$

$C^*$: concentration of acyl-CoA synthetase in an enzyme solution (mg/ml)

(2) Assay method for acyl-CoA oxidase activity:

| | |
|---|---|
| 0.2 M Tris-HCl buffer (pH 8.0) | 0.1 ml |
| 5 mM 4-aminoantipyrine | 0.05 ml |
| 3 mM diethylmetatoluidine | 0.05 ml |
| 0.5 mg/ml peroxidase | 0.05 ml |
| 25 mM palmitoyl-CoA | 0.02 ml |
| distilled water | 0.23 ml |
| Total | 0.50 ml |

An enzyme solution (10 $\mu$l) was added to the above reaction mixture and the mixture was incubated at 37° C. for 10 minutes. The reaction was stopped by adding 4M urea (0.5 ml); and 1% Triton X-100 (2 ml) was added thereto and colorimetric measurement was conducted at 545 nm to measure the amount of hydrogen peroxide formed. One enzyme unit (1 U) is defined as the amount of enzyme which generates 1 $\mu$mole of hydrogen peroxide in one minutes.

The following examples illustrate the present invention but are not to be construed as limiting:

EXAMPLE 1

Production of multi-active enzyme:

Into a 500 ml Erlenmeyer flask, there was introduced an aqueous medium (100 ml) comprising by weight peptone 1.5%, powdered yeast extract 0.5%, KCl 0.2%, NaCl 0.1%, K$_2$HPO$_4$ 0.1%, MgSO$_4$ 0.05% and oleic acid 0.75%, and having a pH of 7.5. A total of 15 flasks each containing the same medium were sterilized at 120° C. and inoculated with *Pseudomonas fragi* B-0771 FERM-P No. 5701 at 30° C., and were shake cultured for 20 hours in a rotary shaker. The combined media were centrifuged at 5000 rpm for 20 minutes to obtain bacterial cells. The cells were added to a lysozyme solution (360 ml, 1.50 mg in 10 mM phosphate buffer, pH 7.0) to obtain a crude solution of multi-active enzyme (340 ml, specific activity: 3.0 U/mg as 3-hydroxyacyl-CoA dehydrogenase activity.)

The isolation and purification of the enzyme were carried out as follows:

Previously-cooled acetone (−20° C., 290 ml) was added to crude multi-active enzyme solution (290 ml) cooled in an ice bath and the precipitate was collected. The precipitate was dissolved in 10 mM Tris-HCl buffer (pH 7.5) containing 1 M KCl and centrifuged at 12,000 rpm for 10 minutes to remove insolubles. The supernatant solution (45 ml) was collected and saturated ammonium sulfate solution (22.5 ml), (pH 7.0) was added thereto. The precipitate was removed by centrifugation at 12,000 rpm for 10 minutes. Further saturated ammonium sulfate solution (28 ml) was added to the supernatant (57 ml). The precipitate was dissolved in 10 mM Tris-HCl buffer (pH 7.5) containing 1 M KCl and dialyzed using a cellophane tube against 10 mM Tris-HCl buffer (pH 7.5, 2.0 lit.) at 4° C. for 20 hours. The dialyzate was lyophilized to obtain a multi-active enzyme powder (77 mg) showing a specific activity of 18.2 U/mg as 3-hydroxyacyl-CoA dehydrogenase activity.

The enzyme (77 mg) dissolved in 20 ml water was charged on a column (3×11 cm) of DEAE-Sephalose CL-6B (Farmacia Co.) equilibrated with 10 mM Tris-HCl buffer and washed with the same buffer. Elution was carried out by linear gradient with 500 ml of 10 mM Tris-HCl buffer and the same buffer containing 0.4 M KCl, at an elution rate of 52 ml/hour. Fractions of 9 ml each were collected and the active fractions Nos. 71–80 (90 ml) showed a specific activity of 30.0 U/mg as 3-hydroxyacyl-CoA dehydrogenase activity. The active fractions were dialyzed against 10 mM phosphate buffer solution (pH 7.5, 2 lit.) and charged on a column (2×10 cm) packed with hydroxyapatite gel. Elution was carried out by linear gradient with 300 ml of 10 mM phosphate buffer (pH 7.5) and 300 ml of 0.5 M phosphate buffer (pH 7.5), at an elution rate of 33 ml/hour. Fractions of 5 ml each were collected and the active fractions were Nos. 46–62 (85 ml) (enoylacyl-CoA hydratase activity: 210.3 U/mg, 3-hydroxyacyl-CoA dehydrogenase activity: 105 U/mg, 3-ketoacyl-CoA thiolase activity: 85.6 U/mg), and were concentrated by ultrafiltration (Amicon Co. XM-50). The concentrate was charged on a column (1.1×90 cm) packed with Toyopeal HW-60 (Toyo Soda Co.) and gel-filtered by 10 mM Tris-HCl buffer, pH 7.5 containing 0.5 M KCl. Fractions of 3.5 ml each were collected and active fractions Nos. 23–27 (17.5 ml) were obtained. The solution was lyophilized to obtain purified multi-active enzyme (20 mg, 110 U/mg as 3-hydroxyacyl-CoA dehydrogenase).

EXAMPLE 2

Thirty liters of the same medium as in Example 1 (to which was added anti-foam silicon KM-72, Shinetsu Chem. Co.) were placed in a 30 lit. jar fermenter and sterilized at 120° C. for 20 minutes. Cultured medium (500 ml) of *Pseudomonas fragi* B-0771 FERM-P No. 5071 was inoculated therein, and the medium was cultured at 30° C., 300 rpm, with 20 l/min. aeration for 17 hours. The cultured medium was centrifuged to obtain the cultured cells. The cells were treated with lysozyme (3 g) in 10 mM phosphate buffer (pH 7.0) to obtain a multi-active enzyme solution (6 lit.) (15.6 U/ml as 3-hydroxyaceyl-CoA dehydrogenase activity).

EXAMPLE 3

Quantitative determination of various fatty acids:
Composition for assay:

| | |
|---|---|
| 0.2 M Pipes-NaOH buffer (pH 7.3) | 0.5 ml |
| 10 mM NAD | 0.2 ml |
| 10 mM MgCl$_2$ | 0.3 ml |
| 10 mM ATP | 0.3 ml |
| 3% Triton X-100 | 0.1 ml |
| 10 mM CoASH | 0.2 ml |
| acyl-CoA synthetase solution (40 U/ml, Toyo Jozo Co.) | 0.02 ml |
| acyl-CoA oxidase (400 U/ml) | 0.02 ml |
| catalase (150 U/ml; Sigma Chem. Co.) | 0.05 ml |
| multi-active enzyme (enoyl-CoA hydratase activity: 400 U/ml; 3-hydroxyacyl-CoA dehydrogenase activity: 200 U/ml; 3-ketoacyl-CoA thiolase activity: 163 U/ml) | 0.05 ml |
| distilled water | 1.25 ml |
| Total | 3.00 ml |

As sample (25 μl) containing 3 mM/ml of fatty acid (0.05 μmole) was added to the above composition for assay (3.00 ml); the mixture was incubated at 37° C. for 5 minutes, and the amount of reduced NAD was measured by absorbency at 340 nm (OD$_{340}$ nm). The results are shown in Table 3. As shown in Table 3, the optical density at 340 nm was proportional to the number of carbons in the fatty acids in the sample.

EXAMPLE 4

Figure 4:
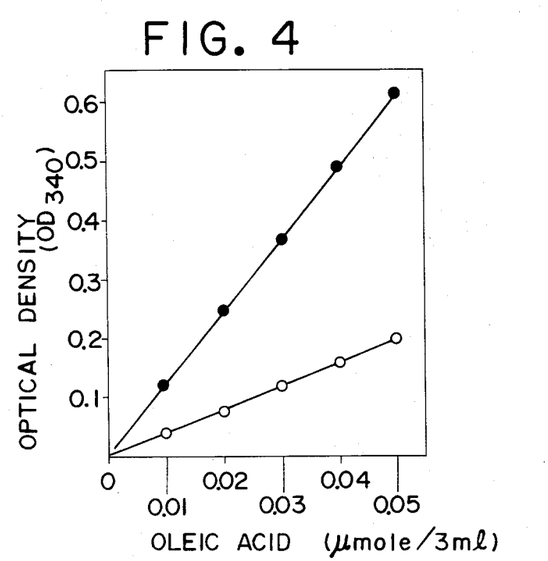
FIG. 4 is a standard assay curve and control curve for oleic acid.

Quantitative assay for oleic acid:

Samples (20 μl each) containing oleic acid (0.01 μmole, 0.02 μmole, 0.03 μmole, 0.04 μmole and 0.05 μmole, respectively) were added to the composition for assay (3.00 ml) in Example 3; each was incubated at 37° C. for 5 minutes, and the amount of reduced NAD was measured by absorbency at 340 nm. The results are shown in FIG. 4 (●—●). In FIG. 4, (○—○) shows the control assay according to the method described in Anal. Biochem., 98, 341 (1979).

As shown in FIG. 4, the assay method of the present invention is superior in sensitivity to conventional prior assay methods.

TABLE 3

| Fatty acid | Carbon numbers (numbers of unsaturated bonds) | OD$_{340nm}$ |
|---|---|---|
| Caproic acid | 6 (0) | 0.089 |
| Caprylic acid | 8 (0) | 0.175 |
| Capric acid | 10 (0) | 0.267 |
| Lauric acid | 12 (0) | 0.356 |
| Myristic acid | 14 (0) | 0.444 |
| Palmitic acid | 16 (0) | 0.530 |
| Palmitoleic acid | 16 (1) | 0.529 |
| Stearic acid | 18 (0) | 0.622 |
| Oleic acid | 18 (1) | 0.628 |
| Linolic acid | 18 (2) | 0.619 |
| Linolenic acid | 18 (3) | 0.630 |

EXAMPLE 5

Assay for oleic acid:
Composition for assay:

| | |
|---|---|
| 0.2 M Pipes-NaOH buffer (pH 7.3) | 0.5 ml |
| 10 mM NAD | 0.2 ml |
| 10 mM MgCl$_2$ | 0.2 ml |
| 10 mM ATP | 0.2 ml |
| 1% Triton X-100 | 0.2 ml |
| 10 mM CoASH | 0.2 ml |
| acyl-CoA synthetase (40 U/ml) | 0.02 ml |
| acyl-CoA oxidase (400 U/ml) | 0.02 ml |
| multi-active enzyme (enoyl-CoA hydratase: 400 U/ml, 3-hydroxyacyl-CoA dehydrogenase: 200 U/ml, 3-ketoacyl-CoA thiolase: 163 U/ml) | 0.01 ml |
| catalase (150 U/ml) | 0.05 ml |
| diaphorase (30 U/ml, Toyo Jozo Co.) | 0.1 ml |
| 0.25% NTB | 0.2 ml |
| distilled water | 1.10 ml |
| Total | 3.00 ml |

Samples (20 μl each) containing oleic acid (0.005 μmole, 0.01 μmole, 0.015 μmole, 0.02 μmole and 0.025 μmole, respectively) were added to the above composition for assay (3.00 ml) and incubated at 37° C. for 10 minutes.

Figure 5:
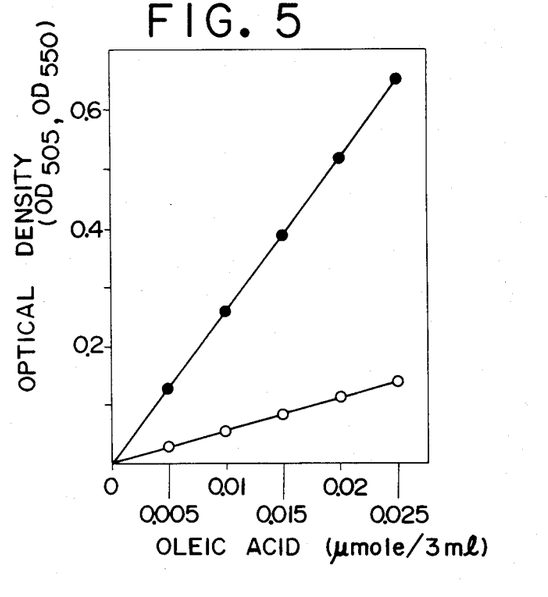
FIG. 5 is another standard assay curve and control curve for oleic acid.

The absorbency at 550 nm of the blue-purple coloration formed, corresponding to the amount of reduced NAD produced according to the reaction, was measured (OD$_{550}$ nm). The results are shown in FIG. 5 (●—●). In FIG. 5, (○—○) shows the control assay according to the method described in Anal. Biochem., 108, 6 (1980) [absorbency at 550 nm, OD$_{505}$ nm].

The results show the present method to be a highly sensitive assay method as compared with the prior art.

EXAMPLE 6

Assay of lipase (serum lipase) activity:
Composition for assay:

| | |
|---|---|
| 0.2 M Pipes-NaOH buffer (pH 7.3) | 0.2 ml |
| 10 mM NAD | 0.15 ml |
| 10 mM MgCl$_2$ | 0.15 ml |
| 10 mM ATP | 0.15 ml |
| 2% Triton X-100 containing 10 mM 1,2-dioleylglyceride | 0.10 ml |
| 10 mM CoASH | 0.15 ml |
| 2 M KCl | 0.1 ml |
| 5% bovine serum albumin | 0.1 ml |
| acyl-CoA synthetase (40 U/ml) | 0.2 ml |
| acyl-CoA oxidase (400 U/ml) | 0.02 ml |
| multi-active enzyme (enoyl-CoA hydratase: 400 U/ml, 3-hydroxyacyl-CoA dehydrogenase: 200 U/ml, 3-ketoacyl-CoA thiolase: 163 U/ml) | 0.05 ml |
| catalase (150 U/ml) | 0.05 ml |
| distilled water | 0.08 ml |

-continued

| | Total | 1.5 ml |
|---|---|---|

The above composition for assay (1.5 ml) was mixed with human serum (50 μl); the mixture was incubated at 37° C., and the formation of reduced NAD was continuously measured at 340 nm. The results are shown in Table 4.

TABLE 4

| Reaction Time (min.) | $OD_{340nm}$ |
|---|---|
| 0 | 0.120 |
| 3 | 0.377 |
| 5 | 0.400 |
| 7 | 0.412 |
| 8 | 0.420 |
| 13 | 0.476 |

According to the above results, it is clear that the fatty acid in the serum was reacted prior to the reaction of the fatty acid liberated from the diglyceride by the action of serum lipase, and the reaction of the free fatty acid in the serum was completed within 7 minutes. The increase of absorbency after the said time was based on reduced NAD which formed from the β-oxidation of the fatty acid liberated from the diglyceride by the action of the serum lipase. Therefore, the lipase activity measured by the increase of absorbency over an interval of 5 mins. from 8 to 13 mins. is 3.44 U/l.

The lipase activity is measured according to the following equation.

Lipase activity (U/l.) = $\Delta OD^* \times \frac{1}{6.2 \times \text{number of } \beta\text{-cycles}} \times \frac{1}{1.5} \times \frac{1000}{50} \times \frac{1}{5} \times 1000$

*ΔOD means that the difference between $OD_{340\,nm}$ after 13 minutes from the start of the reaction and after 8 minutes from the start of the reaction. The number of β-oxidation cycles is 7.

In the serum lipase assay, a composition for assay without adding glyceride is prepared, and samples for assay of serum lipase were added thereto to cancel the effect of free fatty acids in the serum. Then lipase activity can be assayed by adding the above composition for assay without affecting the serum free fatty acid.

EXAMPLE 7

Composition for triglyceride assay:

| | |
|---|---|
| 0.2 M phosphate buffer (pH 7.5) | 0.5 ml |
| 10 mM NAD | 0.3 ml |
| 10 mM MgCl₂ | 0.4 ml |
| 10 mM ATP | 0.3 ml |
| 3% Triton X-100 | 0.1 ml |
| 10 mM CoASH | 0.4 ml |
| acyl-CoA synthetase (40 U/ml) | 0.03 ml |
| acyl-CoA oxidase (400 U/ml) | 0.03 ml |
| multi-active enzyme (enoyl-CoA hydratase: 400 U/ml, 3-hydroxyacyl-CoA dehydrogenase: 200 U/ml, 3-ketoacyl-CoA thiolase: 163 U/ml) | 0.07 ml |
| catalase (150 U/ml) | 0.07 ml |
| lipase (10,000 U/ml, Toyo Jozo Co.) | 0.03 ml |
| distilled water | 0.77 ml |
| Total | 3.00 ml |

The composition for triglyceride assay can be used as follows:

Serum (30 μl) was added to the same composition for assay as in Example 3, which is useful for cancellation of the effect of serum free fatty acids; the mixture was incubated at 37° C. for 10 minutes, and a sample (1 ml, corresponding to serum 10 μl) was collected. The sample was mixed with the above composition for triglyceride assay and the increasing absorbency at 340 nm was measured. Alternatively, the composition for triglyceride assay can be mixed directly with serum (10 μl) and the increasing absorbency at 340 nm after 10 minutes of reaction can be measured.

EXAMPLE 8

Composition for assay of phospholipase $A_1$ activity, phospholipase $A_2$ activity or phospholipase B activity:

In Example 3, distilled water (1.26 ml) in the composition for assay is replaced by 10 mM lecithin solution (0.2 ml) and distilled water (1.06 ml) to prepare a composition for assaying the above enzyme activities.

EXAMPLE 9

Composition for assay of lysophospholipase activity:

In Example 3, distilled water (1.26 ml) was replaced by 10 mM lysolecithin solution (0.2 ml) and distilled water (1.06 ml) to prepare a composition for assaying lysophospholipase activity.

EXAMPLE 10

Composition for assay of phosphatase activity:

In Example 3, distilled water (1.26 ml) was replaced by 10 ml phosphatidate solution (0.2 ml), lipase (10,000 U/ml, 0.05 ml) and distilled water (1.01 ml) to prepare a composition for assaying phosphatase activity.

EXAMPLE 11

Composition for assay of phospholipase C activity:

In Example 7, distilled water (0.77 ml) in the composition for triglyceride assay was replaced by 10 mM lecithin solution (0.2 ml) and distilled water (0.57 ml) to prepare a composition for phospholipase C activity.

The said composition is also affected by glyceride and hence when a sample containing glyceride is used, the amount of fatty acid from the glyceride should be deducted.

EXAMPLE 12

Composition for assay of phospholipase C activity:

A composition for a fatty acid liberating reaction (2.0 ml) comprising 10 mM lecithin soltuion (0.2 ml), lipase (5,000 U/ml, 0.08 ml), 0.2 M phosphate buffer solution (pH 7.5, 0.50 ml) and distilled water (1.22 ml) was prepared.

The said composition and the composition for assay in Example 3 were prepared for assaying phospholipase C activity.

The composition for a fatty acid liberating reaction (2.0 ml) was added to the sample containing phospholipase C (20 μl) and the mixture was incubated at 37° C. for 10 minutes. The composition (3.00 ml) in Example 3 was added thereto; the mixture was incubated at 37° C. for 5 minutes, and the absorbency at 340 nm was measured.

EXAMPLE 13

Composition for assay of phospholipase D activity:

A composition for a fatty acid liberating reaction (2.0 ml) comprising 10 mM lecithin solution (0.2 ml), phosphatidate phosphatase (50 U/ml, Toyo Jozo Co., 0.05 ml), lipase (10,000 U/ml, 0.05 ml), 0.2 M Tris-HCl buffer (pH 7.5, 0.6 ml) and distilled water (1.1 ml) was prepared. The said composition is used together with the composition in Example 3 for the composition for the assay of phospholipase D.

EXAMPLE 14

Composition for assay of choline esterase activity:
In Example 3, distilled water (1.26 ml) was replaced by 2 mM palmitoyl-choline ester solution (0.2 ml) and distilled water (1.06 ml) to prepare a composition for the assay of choline esterase activity.

EXAMPLE 15

Composition for assay of cholesterol esterase activity:
In Example 3, distilled water (1.26 ml) was replaced by 5 mM 3-oleoyl-cholesterol ester solution (0.2 ml) and distilled water (1.06 ml) to prepare a composition for the assay of cholesterol esterase activity.

EXAMPLE 16

Composition for assay of lecithin cholesterol acyl transferase activity:
A composition for a fatty acid liberating reaction (2.1 ml) comprising 5 mM cholesterol solution (0.2 ml), 5 mM lecithin solution (0.2 ml), lysophospholipase (80 U/ml, 0.05 ml) and 0.3% Triton X-100 in 0.1 M phosphate buffer (pH 7.5, 1.55 ml) was prepared.
The said composition together with the composition in Example 3 is used for the assay of lecithin cholesterol acyl transferase activity.

EXAMPLE 17

Composition for assay of cholesterol ester:
In Example 3, distilled water (1.26 ml) was replaced by cholesterol esterase (350 U/ml, Toyo Jozo Co., 0.2 ml) and distilled water (1.06 ml) to prepare a composition for the assay of cholesterol ester.

EXAMPLE 18

A method for the production of acyl-CoA oxidase can be as follows:
An aqueous medium (10 ml) containing by weight oleic acid 1%, yeast extract 0.25%, peptone 1%, KCl 0.2%, $K_2HPO_4$ 0.1%, $MgSO_4 \cdot 7H_2O$ 0.05% and antifoaming agent (Disfoam BC-51Y) 0.2% was introduced into a test tube after sterilization. *Arthrobacter* sp. B-0720 FERM-P No. 5224 was inoculated thereinto and the medium cultured at 30° C. overnight with shaking. The said culture was transferred into the same medium (5 lit.) in a 8 lit. jar fermenter and submerged aeration cultured at 30° C. for 20 hours, 600 rpm with 5 lit./min. aeration. The cultured cells were collected by centrifugation and suspended in 10 mM phosphate buffer (pH 7.0), 2 mM EDTA and 0.5 mg/ml lysozyme, then the suspension was stirred at 37° C. for 60 minutes. DNAase (5 mg) was added thereto, and the mixture was tirred for 10 minutes and centrifuged at 10,000 rpm for 20 minutes.
Acetone (200 ml) was added to the supernatant, and the material was centrifuged and acetone (1.8 lit.) was again added. The precipitate obtained by centrifugation was dissolved in 10 mM phosphate buffer (pH 7.0, 200 ml). The insolubles were removed by centrifugation and saturated ammonium sulfate solution was added to the supernatant to 30–75% saturation. The precipitate, dissolved in 10 mM phosphate buffer (pH 7.0, 40 ml), was desalted by charging on a column of acrylamide gel (Biogel P-2, Biorad Co.) It was then charged on a column of calcium phosphate gel, washed, and eluted by linear gradient elution with 0.05–0.5 M phosphate buffer (pH 7.0). The active fractions (around 0.45 M) were collected, concentrated by ultrafiltration (Diaflow membrane PM-10, Amicon Co.), and lyophilized to obtain acyl-CoA oxidase (specific activity: 5.5 U/mg, total activity: 850 U, yield: 8.5%).

What is claimed is:
1. An assay method for a fatty acid component in a sample, which fatty acid is originally present in the sample or is liberated from a fatty acid ester in the sample, comprising:
   (a) converting the fatty acid to acyl-CoA;
   (b) converting the thus-produced acyl-CoA to dehydroacyl-CoA;
   (c) converting the thus-produced dehydroacyl-CoA to hydroxyacyl-CoA;
   (d) converting the thus-produced hydroxyacyl-CoA to ketoacyl-CoA;
   (e) converting the thus-produced ketoacyl-CoA to acyl-CoA; and measuring the detectable changes in the reaction mixture, wherein steps (c), (d) and (e) utilize the enzyme activity of a multi-active enzyme comprising enoyl-CoA hydratase activity, 3-hydroxyacyl-CoA dehydrogenase activity and 3-ketoacyl-CoA thiolase activity in a single enzyme protein, said multi-active enzyme being an enzyme obtained from a multi-active-enzyme-producing mircroorganism strain *Pseudomonas fragi* B-0771 FERM-P No. 5601.

2. An assay method according to claim 1 wherein the reagents in the respective steps are
   (a) fatty acid, CoASH, ATP or GTP and acyl-CoA synthetase activity;
   (b) acyl-CoA, oxygen and acyl-CoA oxidase activity;
   (c) dehydroacyl-CoA, water and enoyl-CoA hydratase activity;
   (d) hydroxyacyl-CoA, NAD and 3-hydroxyacyl-CoA dehydrogenase activity; and
   (e) ketoacyl-CoA, CoASH and 3-ketoacyl-CoA thiolase activity.

3. An assay method according to claim 1 wherein the step of measuring the detectable changes is a process for quantitative determination of the amount of reduced NAD which forms in the reaction mixture.

4. An assay method according to claim 3 wherein the said quantitative determination of the amount of reduced NAD is performed by wavelength in the absorption wavelength region of the specific absorption wavelength for reduced NAD.

5. An assay method according to claim 4 wherein the said wavelength in the absorption wavelength region is approximately 320 nm–360 nm.

6. An assay method according to claim 5 wherein the said wavelength in the absorption wavelength region is approximately 340 nm.

7. An assay method according to claim 4 wherein the said quantitative determination of the amount of reduced NAD is performed by colorimetry with a hydrogen atom transfer chromogen as an acceptor of hydrogen atom of reduced NAD.

8. An assay method according to claim 7 wherein the said hydrogen atom transfer chromogen is a hydrogen atom transfer system which contains diaphorase and a water-soluble tetrazolium salt.

9. An assay method according to claim 1 wherein the component in the sample to be assayed is originally in the form of a fatty acid.

10. An assay method according to claim 1 wherein the said fatty acid in the sample to be assayed is a fatty acid liberated from a fatty acid ester by enzyme activity which generates fatty acid from fatty acid ester.

11. An assay method according to claim 10 wherein the said assay is an assay of fatty acid ester or an assay of enzyme activity.

12. An assay method according to claim 10 wherein the said fatty acid ester is a monoglyceride, a diglyceride or a triglyceride, and the enzyme activity is lipase activity.

13. An assay method according to claim 12 wherein the said lipase activity assay is performed by adding albumin.

14. An assay method according to claim 10 wherein the said fatty acid is lecithin and the enzyme activity is phospholipase $A_1$ activity, phospholipase $A_2$ activity or phospholipase B activity.

15. An assay method according to claim 10 wherein the said fatty acid ester is lysolecithin and the enzyme activity is lysophospholipase activity.

16. An assay method according to claim 10 wherein the said fatty acid ester is phosphatidic acid and the enzyme activity is phosphatidic acid phosphatase activity and lipase activity.

17. An assay method according to claim 10 wherein the said fatty acid ester is lecithin and the enzyme activity is phospholipase C activity and lipase activity.

18. An assay method according to claim 10 wherein the said fatty acid ester is lecithin and the enzyme activity is phospholipase D activity, phosphatidic acid phosphatase activity and lipase activity.

19. An assay method according to claim 10 wherein the said fatty acid ester is acylcholine and the enzyme activity is choline esterase activity.

20. An assay method according to claim 10 wherein the said fatty acid ester is sterol ester and the enzyme activity is cholesterol esterase activity.

21. An assay method according to claim 1 wherein the said fatty acid is liberated from a sample comprising lecithin and cholesterol by the enzyme activity of lecithin:cholesterol acyltransferase activity or lysophospholipase activity.

22. An assay method according to claim 21 wherein the said assay is for assaying lecithin, cholesterol or enzyme activity.

23. A process for the production of an enzyme, which comprises culturing the microorganism strain *Pseudomonas fragi* B-0771 Ferm-P No. 5701 to produce an enzyme having enoyl-CoA hydratase activity, 3-hydroxyacyl-CoA dehydrogenase activity and 3-ketoacyl-CoA thiolase activity, and isolating the enzyme thus produced from the culture medium.

* * * * *